United States Patent
Sakaida et al.

(10) Patent No.: US 7,903,854 B2
(45) Date of Patent: Mar. 8, 2011

(54) IMAGE TRANSMISSION METHOD, IMAGE TRANSMISSION APPARATUS, AND IMAGE TRANSMISSION PROGRAM

(75) Inventors: Hideyuki Sakaida, Tokyo (JP); Shinichi Takeyama, Tokyo (JP); Takuma Sakamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 883 days.

(21) Appl. No.: 11/834,295

(22) Filed: Aug. 6, 2007

(65) Prior Publication Data

US 2008/0037849 A1     Feb. 14, 2008

(30) Foreign Application Priority Data

Aug. 9, 2006 (JP) ................................. 2006-216749

(51) Int. Cl.
*G06K 9/00* (2006.01)
*A61B 6/00* (2006.01)
(52) U.S. Cl. ............................ 382/128; 382/305; 378/21
(58) Field of Classification Search .................. 382/128, 382/100, 129, 130, 131, 132, 133, 134, 155, 382/168, 181, 190, 232, 254, 260, 274, 275, 382/276, 305, 312; 1/1; 600/459; 705/2; 378/4, 20, 21; 707/999.002

See application file for complete search history.

(56) References Cited

U.S. PATENT DOCUMENTS

| | | | | |
|---|---|---|---|---|
| 5,758,649 | A * | 6/1998 | Iwashita et al. | 600/459 |
| 6,678,703 | B2 * | 1/2004 | Rothschild et al. | 1/1 |
| 7,624,027 | B1 * | 11/2009 | Stern et al. | 705/2 |
| 7,689,539 | B2 * | 3/2010 | Sjoblom et al. | 707/999.002 |
| 7,729,928 | B2 * | 6/2010 | Backhaus et al. | 705/2 |

FOREIGN PATENT DOCUMENTS

| | | |
|---|---|---|
| JP | 2002-253539 A | 9/2002 |
| JP | 2006-006449 A | 1/2006 |

* cited by examiner

*Primary Examiner* — Seyed Azarian
(74) *Attorney, Agent, or Firm* — Sughrue Mion, PLLC

(57) ABSTRACT

Volume data formed of tomographic images (medical images) is stored in a storage unit of a data center. Recorded in a tag area of each tomographic image is site information indicating the site contained in each tomographic image. A data server of the data center reads the volume data from the storage unit in response to a transmission request from a medical facility. Then, the data server extracts from the volume data the tomographic images of the same site as designated by the transmission request. The data server transmits the extracted tomographic images to the medical facility which made the transmission request.

10 Claims, 7 Drawing Sheets

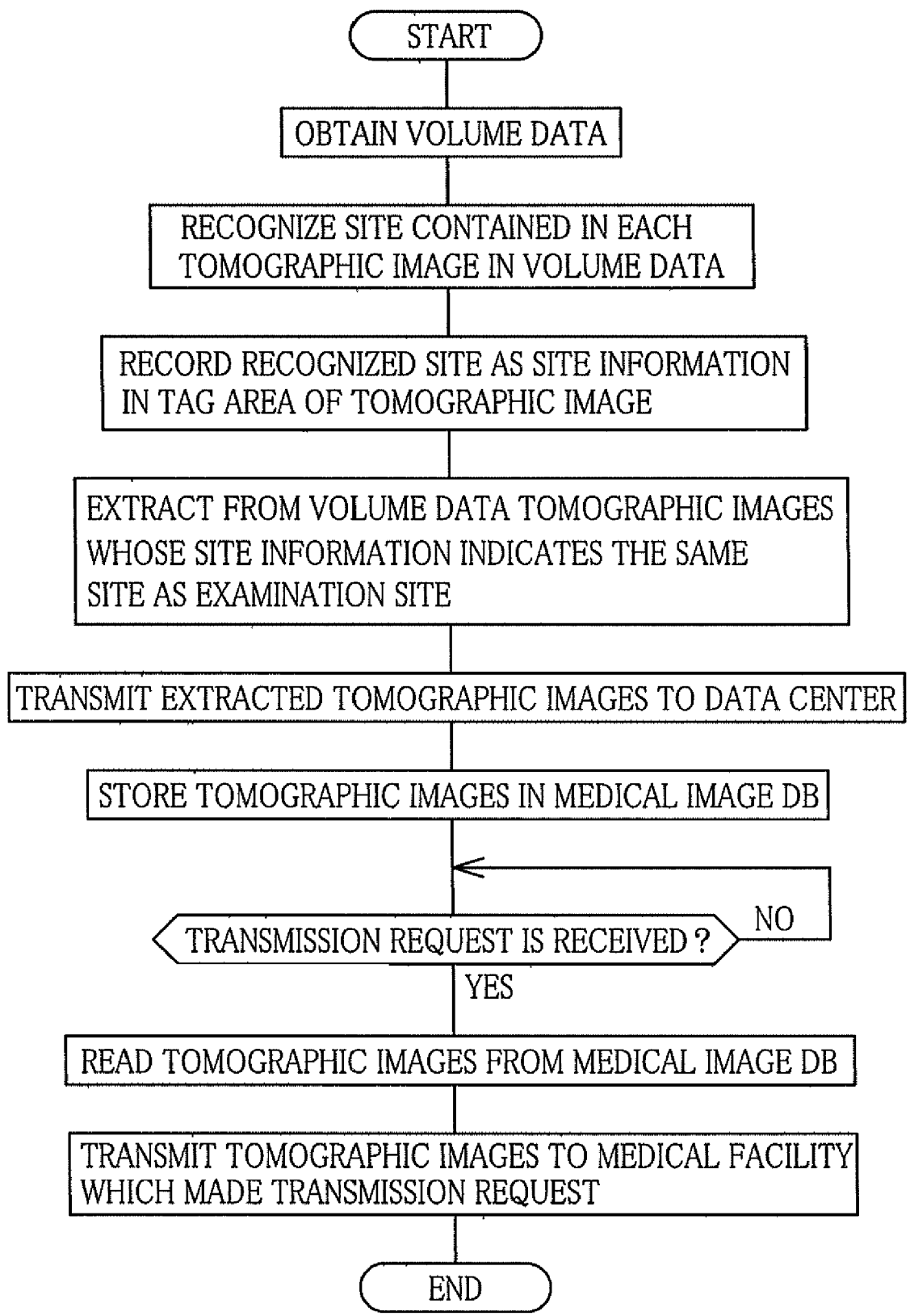

IMAGE TRANSMISSION METHOD, IMAGE TRANSMISSION APPARATUS, AND IMAGE TRANSMISSION PROGRAM

FIELD OF THE INVENTION

The present invention relates to an image transmission method, an image transmission apparatus, and an image transmission program to transmit only medical images containing a desired site out of a group of medical images.

BACKGROUND OF THE INVENTION

Various modalities such as CR (Computed Radiography) devices, CT (Computed Tomography) devices, MRI (Magnetic Resonance Imaging) devices, PET (Positron Emission Tomography) devices, and ultrasonic diagnosing devices are pervasive in medical facilities such as clinics and hospitals. Medical images taken with such modalities play an important role in diagnosing patients.

Conventionally, to obtain tomographic images of a patient as medical images using the CT device, the MRI device, or the like, a doctor previously designates a site, for example, head, thorax, abdomen, or the like in accordance with symptoms of a patient, and only tomographic images containing the designated site are taken. However, due to a setting error of an operator, a mismatch between the designated site and the site contained in the taken image sometimes occurs. In such cases, it becomes necessary to take the tomographic image again which imposes an additional burden to the patient and may also hinder the diagnosis. Moreover, if the modality is a CT device or the like using X-ray, the patient will be exposed to an additional dose of radiation.

Recently, however, due to increases in scan speed and capacity of a recording device, a wide range scan of the patient such as whole body CT scan is carried out at a time without designating a site at each examination. If the whole body CT scan of the patient is carried out, the desired site is included in the obtained tomographic images without fail. Therefore, the above described mismatch is surely prevented.

A large number of tomographic images is obtained when a wide range scan such as whole body CT scan is carried out. If the tomographic images are stored in film, a storage space, management and retrieval thereof puts a large burden on the medical facility. To solve such problems, a system which makes various information in the medical facility electronically available is disclosed in, for example, Japanese Patent Laid-Open Publication No. 2006-006449. In such a system, the medical images taken in the medical facility are digitized and stored in the server. Thus, a storage space of the medical images in the medical facility is significantly reduced. In addition, using the server to manage and search for the medical images improves operation efficiency of the medical facility.

The server transmits the stored medical images to a viewer terminal or the like when a doctor interprets the medical images or uses the medical images for explanation to the patient. However, a transmission time may become excessively long to transmit the large number of the tomographic images obtained by a wide range scan such as the whole body CT scan. The doctor and the patient just have to wait during the transmission time of tomographic images, and the long waiting time may make them uncomfortable. To avoid such problem, medical images are transmitted on a predetermined time or data amount basis so as to control the waiting time (see the Japanese Patent Laid-Open Publication No. 2006-006449).

However, the transmitted tomographic images do not always contain the desired site when the tomographic images are transmitted on a predetermined time or data amount basis as disclosed in the Japanese Patent Laid-Open Publication No. 2006-006449. If the transmitted tomographic images do not contain the desired site, it is necessary to repeat the transmission. Thus, operation becomes complicated and time-consuming.

If the tomographic images obtained by the wide range scan are transmitted from the server, much time and manpower is necessary to search for the tomographic images containing a desired site. As a related technology, Japanese Patent Laid-Open Publication No. 2002-253539 discloses a method to automatically recognize a site contained in a medical image using image analysis. However, the above method recognizes the medical image one by one, and does not refer to collective processing of the medical images and collective transmission of the medical images to other devices.

SUMMARY OF THE INVENTION

In view of the foregoing, an object of the present invention is to provide an image transmission method, an image transmission apparatus, and image transmission program capable of efficiently transmitting only desired medical images containing a target site out of a group of medical images.

In order to achieve the above and other objects, the image transmission method according to the present invention includes the following steps: (a) recognizing a site contained in each medical image, (b) generating site information indicating a site contained in each medical image based on a result of the recognizing step, (c) extracting the desired medical images whose site information indicates the same site as the target site, and (d) transmitting the desired medical images to a designated destination.

It is also possible to provide the following steps between the step (b) and the step (c): storing the group of the medical images and the site information in a storage unit, and reading the group of the medical images and the site information from the storage unit in response to an instruction for the transmission.

It is also possible to provide the following steps before the step (a): storing the group of the medical images in a storage unit, and reading the group of the medical images and the site information from the storage unit in response to the instruction for the transmission.

It is also possible to provide the following steps between the step (c) and the step (d): storing the medical images extracted in the step (c) in a storage unit; and reading the extracted medical images from the storage unit in response to the instruction for the transmission.

It is preferable to concurrently input the target site with the instruction for the transmission. The target site may be an examination site input as order information at the time of taking the group of the medical images.

In the step (a), it is preferable that the site is automatically recognized by image analysis of each the medical images.

In the step (b), it is preferable that the site information is attached to the corresponding medical image as metadata.

It is preferable that the site includes head, thorax, abdomen, pelvis, legs, and organs such as brain, heart, lungs, liver and stomach.

An image transmission apparatus according to the present invention includes a recognizing section for recognizing a site contained in each medical image, a site information generating section for generating site information indicating a site contained in medical image based on a result from the recognizing section, an extracting section for extracting medical images whose site information indicates the same site as the target site, and a transmitting section for transmitting the extracted medical images to a designated destination.

An image transmission program according to the present invention directs a computer to execute the following steps: (a) recognizing a site contained in each medical image, (b) generating site information indicating a site contained in each medical image based on a result of the recognizing step, (c) extracting medical images whose site information indicates the same site as the target site, and (d) transmitting the extracted medical images to a designated destination.

According to the present invention, the site contained in each medical image is recognized, and the site information indicating the site contained in each medical image is generated based on the recognition result, and the medical images whose site information indicates the same site as the target site are extracted out of the group of medical images. Thus, only the desired medical images containing the target site are efficiently transmitted. As a result, it becomes possible to save the waiting time and inconvenience of searching the medical images containing the target site.

BRIEF DESCRIPTION OF THE DRAWINGS

The above objects and advantages of the present invention will become more apparent from the following detailed description when read in connection with the accompanying drawings, in which:

FIG. 8 is a flowchart showing an example in which only extracted tomographic images are stored.

DETAILED DESCRIPTION OF THE PREFERRED EMBODIMENTS

Figure 1:
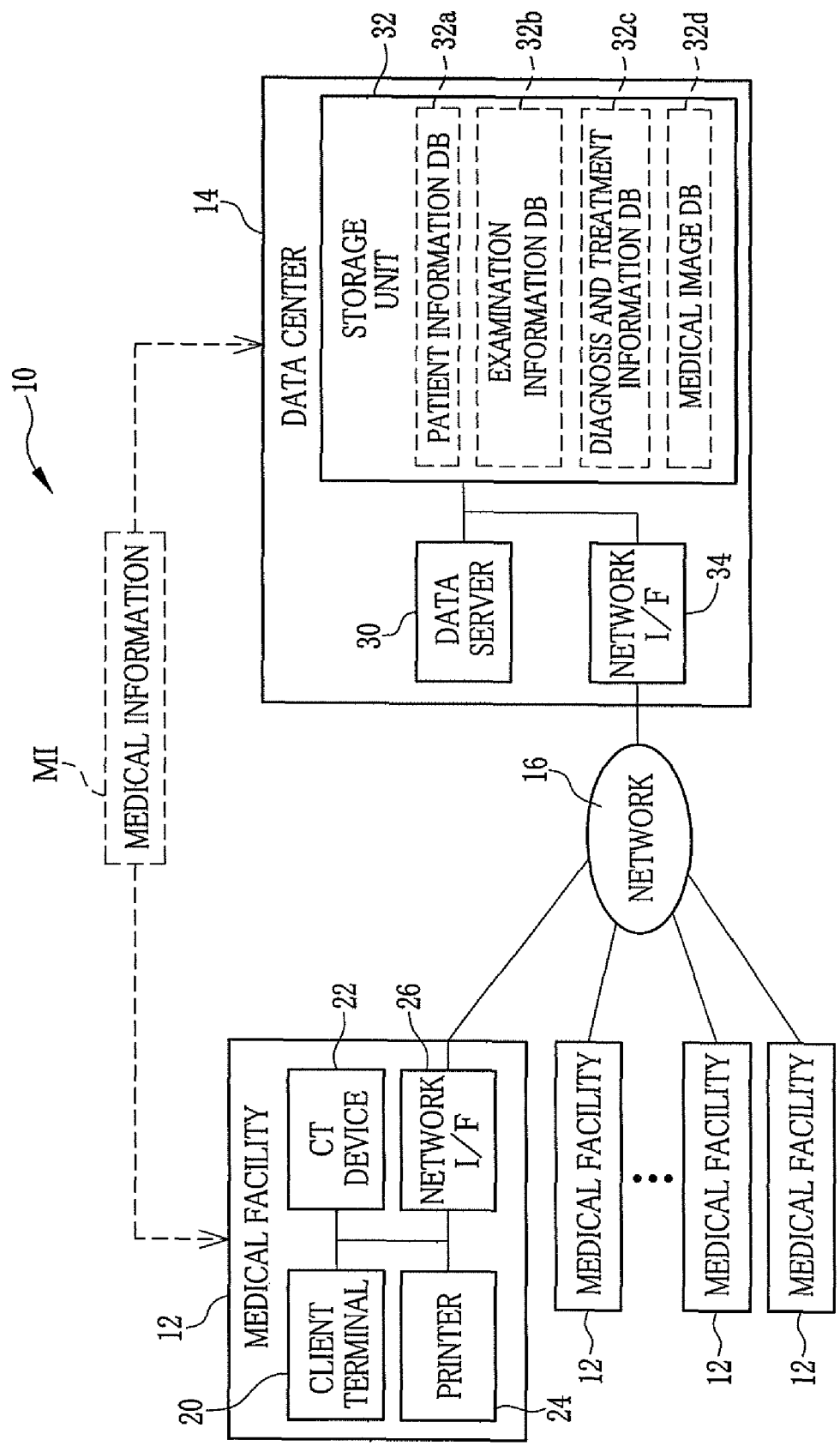
FIG. 1 is an explanatory view schematically showing a configuration of a medical network system.

In FIG. 1, a medical network system 10 is constituted of medical facilities 12 such as hospitals and clinics, and a data center (image transmission apparatus) 14 to which each medical facility 12 is connected via a network 16. Each medical facility 12 transmits to the data center 14 via the network 16 various medical information MI such as outpatient information and medical images obtained for the diagnoses. The data center 14 stores the medical information MI transmitted from each medical facility 12 and transmits back the stored medical information MI in response to a transmission request from the medical facility 12.

The data center 14 of the medical network system 10 centrally manages the medical information MI obtained in each medical facility 12 in electronic data form, so that a storage space for patient charts and films of medical images in each medical facility 12 is saved. Management and search of the medical information MI by the data center 14 improves operation efficiency of the medical facility 12. The medical network system 10 allows the shared use of the medical information MI by the medical facilities 12 via the data center 14, and strengthens the cooperation among the medical facilities 12.

Provided in the medical facility 12 are a client terminal 20, a CT device 22, a printer 24, and a network interface 26. The client terminal 20 manages the medical information MI in the medical facility 12. The CT device 22 takes tomographic images of a patient as medical images. The printer 24 prints various electronic data including the medical images on paper, films, or the like. The network interface 26 connects the medical facility 12 to the network 16. These devices are connected to each other via a local area network (LAN) within the medical facility 12.

In FIG. 1, one client terminal 20, one CT device 22, and one printer 24 are disposed in each medical facility 12. However, plural client terminals 20, the CT devices 22, and/or the printers 24 may be disposed in each medical facility 12. Note that the configuration of each medical facility 12 connected to the data center 14 is not limited to the above. For example, a medical facility 12 having other modalities such as the CR device and the MRI device, or that without the above modalities may be connected to the data center 14.

The client terminal 20 is disposed, for example, in a consultation room in the medical facility 12. The client terminal 20 is used for inputting medical information MI of the patient. A doctor inputs the medical information MI via the client terminal 20 while, for example, seeing the patient. Moreover, the client terminal 20 displays the tomographic images taken with the CT device 22, various medical information MI read from the data center 14, and the like, which assist the doctor in description of the diagnosis.

The medical information MI input by the doctor includes, for example, patient information, examination information, and diagnosis and treatment information. The patient information is personal information of each patient and includes, for example, patient name, patient ID, present address, date of birth, age, gender, family structure, past medical history, allergy, and the like. The patient ID is a unique number assigned to the patient, and automatically issued by the client terminal 20 at the time of inputting the patient information. The patient ID is, for example, an 8-digit number having a 4-digit medical facility number and a 4-digit serial number to avoid overlaps between the medical facilities 12. The issuing methods and the number of digits of the patient ID are not limited to the above. For example, it is also possible to use serial numbers issued by the data center 14. Moreover, the patient ID is not limited to the combination of numbers. For example, it is also possible to combine letters in alphabet and signs with the numbers to create the patient ID.

The examination information is information related to medical images taken for diagnosis, and includes, for example, examination date, device used for examination, examination method, and examination site. The examination method includes an orientation of the patient at the time of the examination such as to the front or to the side, and whether a contrast medium is used for the examination. The examination site is a site to be examined in the examination, for example, head, thorax, abdomen, pelvis, legs, partly overlapping sites such as head and neck, thorax and abdomen. The diagnosis and treatment information is information of diagnosis and treatment provided to the patient, and includes, for example, examination date, medical department, name of illness or injury, diagnosis, period of treatment, medication and dosage, and pharmacy name. The period of treatment is a period during which the patient visited the medical facility 12 for treatment of a single illness or injury.

Instead of using the client terminal 20, the patient information may be input using, for example, a medical billing computer (not shown) which creates and records certificates of medical remuneration. The examination information may be input, for example, using the CT device 22 instead of using the client terminal 20 at the time of taking the tomographic images. It is also possible to integrate various information of the patient without sorting.

The CT device 22 takes the tomographic images of the patient based on order information input via the client terminal 20. The order information includes, for example, the patient information of the patient to be examined, doctor information of the doctor requesting the examination, and the scheduled date of the examination. The doctor information includes name, medical department, and contact number of the doctor.

Figure 2:
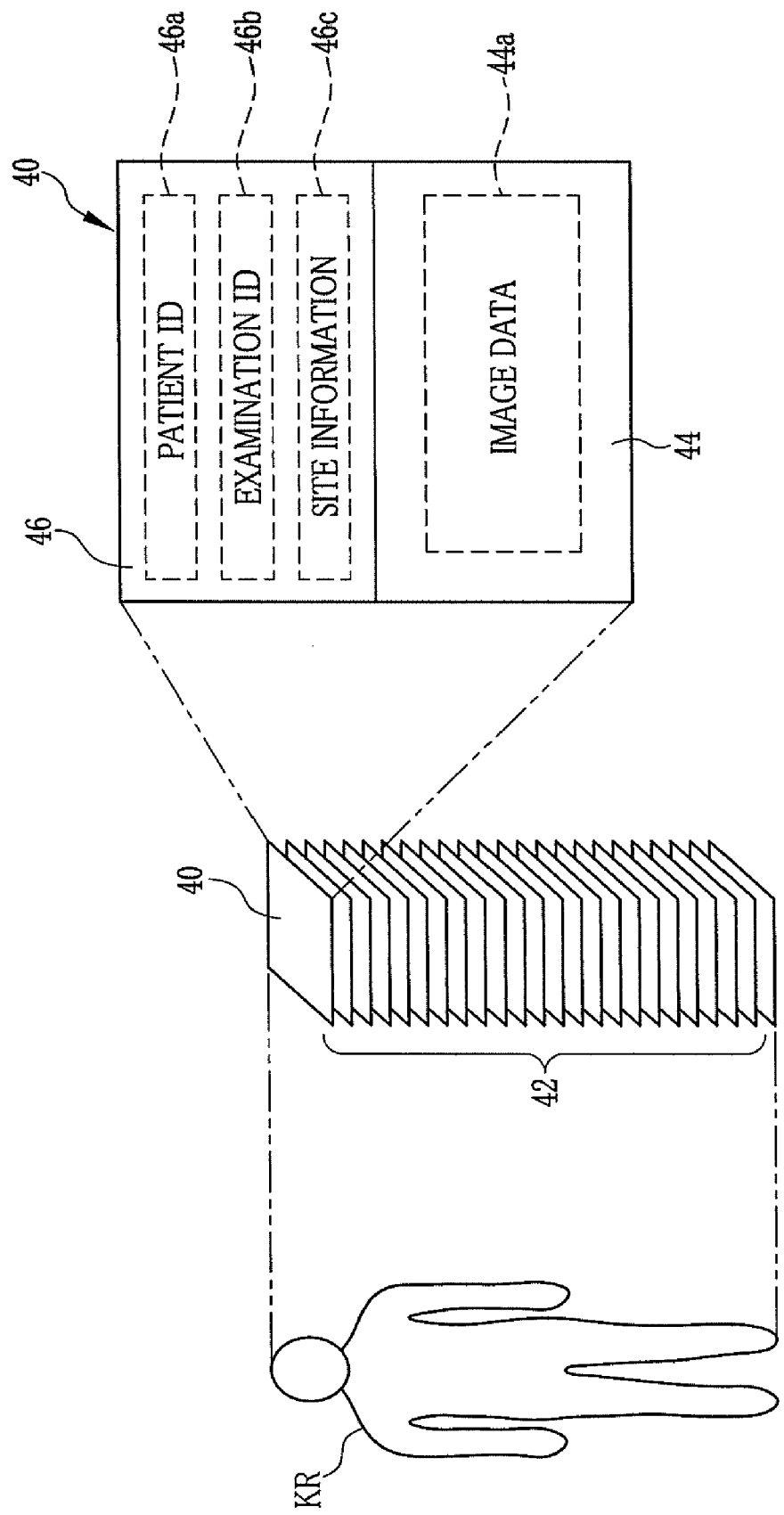
FIG. 2 is an explanatory view schematically showing a configuration of volume data and tomographic images.

As shown in FIG. 2, the CT device 22 carries out the whole body CT scan of a patient KR and obtains plural tomographic images 40 at a time in accordance with settings such as slice thickness. The obtained tomographic images are organized on an examination-by-examination basis and stored in the data center 14 or the like. Hereinafter, a set of tomographic images obtained in one examination is called volume data 42.

As shown in FIG. 2, each tomographic image 40 has an image recording area 44 to record image data 44a, and a tag area 46 to record metadata. Various information such as, for example, a patient ID 46a, an examination ID 46b, and site information 46c is recorded as the metadata in the tag area 46 of the tomographic image 40. The patient ID 46a is used for identifying the patient KR in the tomographic images 40. The examination ID 46b is, for example, a unique number assigned to tomographic images 40 at every examination. The examination ID 46b specifies the examination in which the tomographic images 40 are taken, and is used to organize and store the tomographic images 40 as the volume data 42. The volume data 42 of the patient KR includes tomographic images 40 of the whole body from head to toe. The site information 46c indicates the site contained in each tomographic image 40.

Each metadata is recorded using the client terminal 20 or at the data center 14, for example, concurrently with generating the image data at the time of taking the tomographic images 40, or after taking the tomographic images 40. The metadata recorded in the tag area 46 is not limited to the above. Any type of information can be recorded as the metadata as long as it makes the identification of the tomographic image 40 possible. As a file format for medical images having the above described tag area 46, for example, DICOM (Digital Imaging and Communications) is known.

Returning to FIG. 1, the network interface 26 converts the data between a format corresponding to the LAN within the medical facility 12 and that corresponding to the network 16, and thus connects the LAN and the network 16. The network interface 26 is, for example, a modem or a router, and selected in accordance with specification of the LAN and the network 16. The network 16 can be of any type, for example, dedicated lines, PSTN (public switched telephone network), or Internet as long as intercommunication between each medical facility 12 and the data center 14 is possible.

The data center 14 is provided with a data server 30, a storage unit (memory device) 32, and a network interface (transmitting section) 34. The data server 30 controls transmission and reception of medical information MI to/from each medical facility 12. The storage unit 32 stores the medical information MI transmitted from each medical facility 12. The network interface 34 is used for connecting the data center 14 to the network 16. Each section is interconnected via the LAN within the data center 14.

The data server 30 sorts the medical information MI received from each medical facility 12 into information items such as the patient information, the examination information, the diagnosis and treatment information, and the medical images, and stores each information item in the storage unit 32. In response to the transmission request from each medical facility 12, the data server 30 reads the stored information items from the storage unit 32, and transmits the medical information MI to the medical facility 12 which made the transmission request. At the time of transmission and the reception of the medical information MI to/from the medical facility 12, the data server 30 checks, for example, the medical facility number, the doctor ID number assigned to each doctor, or a digital certificate previously issued to each client terminal 20 to restrict unauthorized access to the data center 14.

The storage unit 32 is of a so-called network compatible type. The storage unit 32 is constituted of, for example, various drives to record information in media such as a DVD, or a hard disk drive (HDD). It is also possible to provide plural storage units 32 and use them as, for example, a main storage unit and a backup storage unit. The storage unit 32 may be a collection of plural drives each of which corresponds to, for example, information item of the medical information MI to be recorded. The storage unit 32 is not limited to the network compatible type. For example, an HDD 62 (see, FIG. 4) of the data server 30 may be used as the storage unit 32.

Constructed in the storage unit 32 are plural data bases such as a patient information data base (DB) 32a, an examination DB 32b, a diagnosis and treatment information DB 32c, and a medical image DB 32d which correspond to the information items of the medical information MI. The patient information DB 32a stores the patient information transmitted from each medical facility 12. The examination information DB 32b, the diagnosis and treatment information DB 32c, the medical image DB 32d respectively store the examination information, the diagnosis and treatment information, and medical images transmitted from each medical facility 12.

The network interface 34 connects the LAN of the data center 14 to the network 16 by converting the data between a format corresponding to the LAN of the data center 14 and that corresponding to the network 16. The network interface 34 is, for example, a modem or a router, and selected in conformity with the specifications of the LAN and the network 16.

Figure 3:
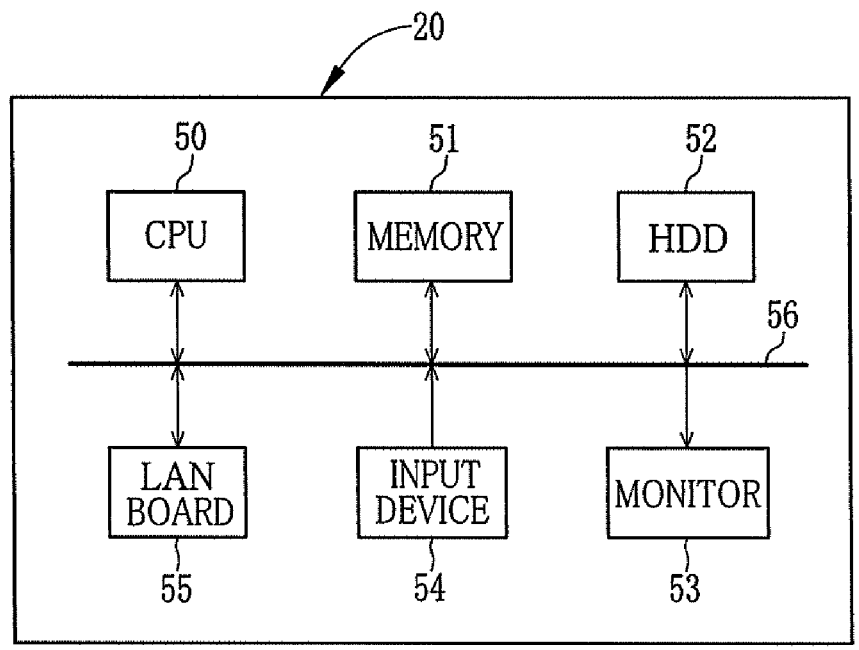
FIG. 3 is a block diagram schematically showing a configuration of a client terminal.

In FIG. 3, the client terminal 20 is a known personal computer, a workstation, or the like, and has a CPU 50, a memory 51, an HDD 52, a monitor 53, an input device 54, and a LAN board 55. These elements are connected to each other via a bus 56. Various programs corresponding to the medical network system 10 are stored in the HDD 52. The CPU 50 reads each program from the HDD 52 and expands the program in the memory 51, and sequentially executes the program. Thus, the CPU 50 integrally controls the client terminal 20.

The monitor 53 displays various display screens in accordance with processing of program executed by the CPU 50. A known display device, for example, an LCD, a CRT display or the like can be used as the monitor 53. The input device 54 is constituted of, for example, a key board and a mouse, and used for instructing the client terminal 20 to carry out operation and inputting medical information MI. The LAN board 55 connects the client terminal 20 to the LAN of the medical facility 12. The LAN board 55 is selected to be in conformity with the specification of the LAN such as, for example, Ethernet®.

Figure 4:
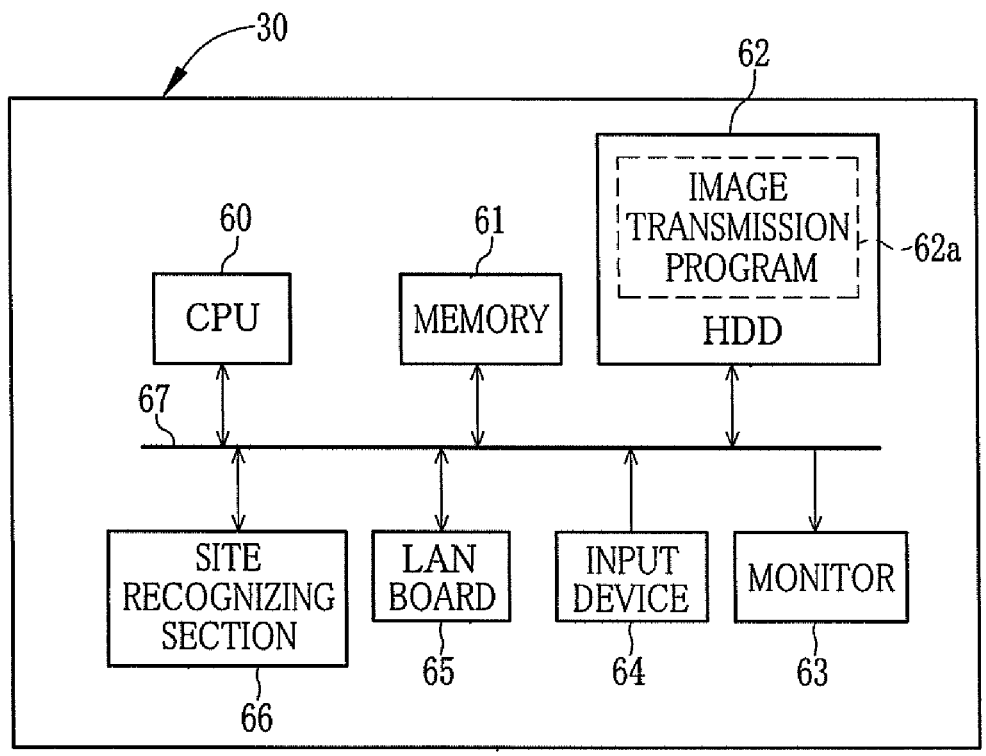
FIG. 4 is a block diagram schematically showing a configuration of a data server.

In FIG. 4, the data server 30 is a known personal computer, a workstation, or the like, and has a CPU (extracting section) 60, a memory 61, the HDD 62, a monitor 63, an input device 64, a LAN board 65, and a site recognizing section (recognizing section, site information generating section) 66. These elements are connected to each other via a bus 67. The HDD 62 stores various programs including an image transmission program 62a. The CPU 60 reads each program from the HDD 62 and expands it in the memory 61, and sequentially executes the program. Thus, the CPU 60 integrally controls the data server 30.

Since the monitor 63, the input device 64, and the LAN board 65 are similar to those provided in the client terminal 20, the detailed descriptions are omitted. The monitor 63 and the input device 64 are used, for example, when an administrator of the data center 14 updates each program stored in the HDD 62 and information stored in each of the data bases 32a, 32b, 32c, and 32d constructed in the storage unit 32.

The site recognizing section 66 performs image analysis of the input medical image and recognizes the site contained therein. The image analysis is performed by, for instance, calculating a feature quantity of the image based on the CT value of each pixel, and comparing and matching the calculated feature quantity with the previously stored feature quantity of each site.

Figure 5:
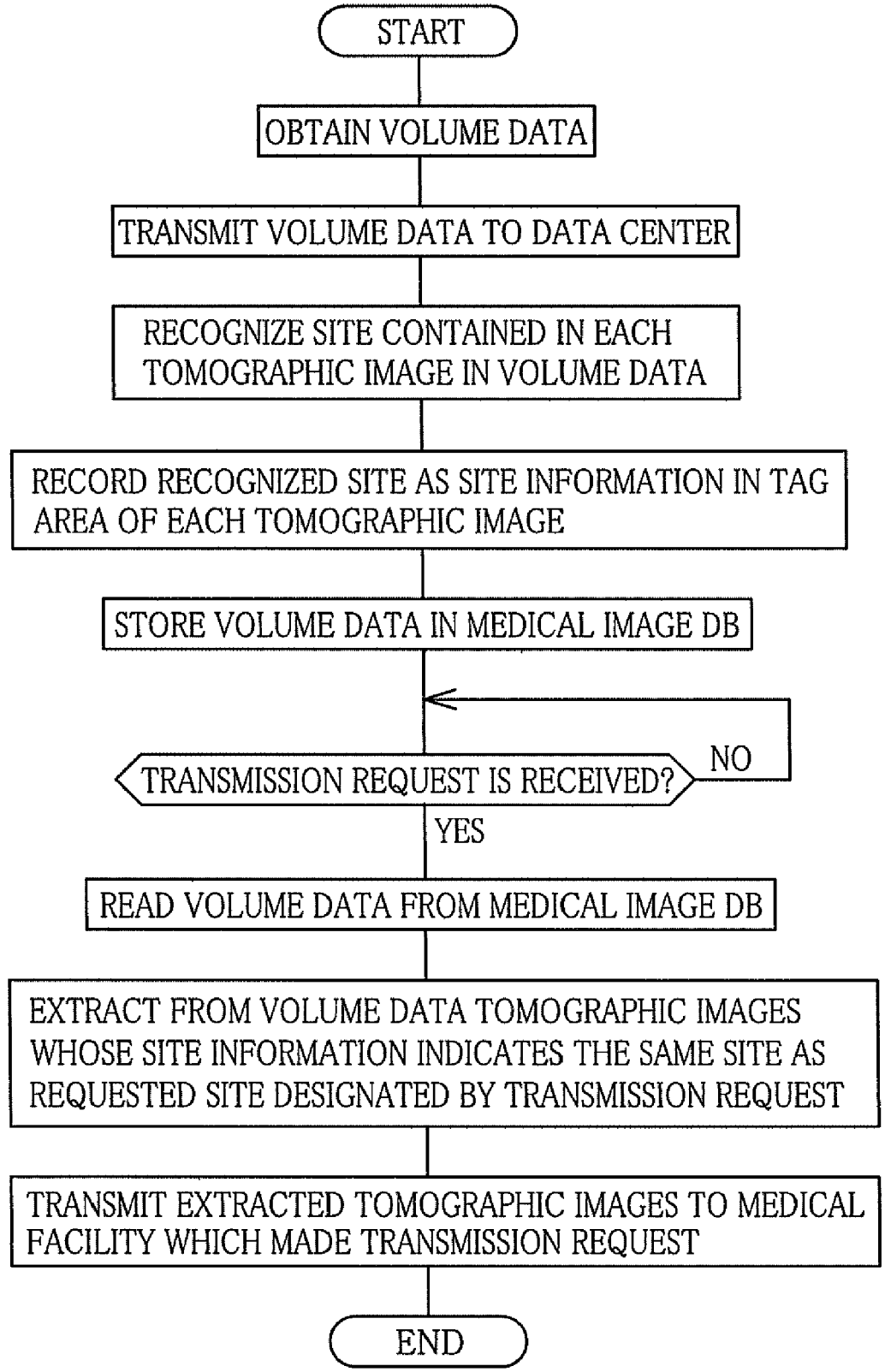
FIG. 5 is a flowchart schematically showing operation of a medical network system.

Next, referring to a flowchart in FIG. 5, the operation of the medical network system 10 with the above configuration is described. The CT device 22 takes tomographic images of the patient KR based on the order information input from the client terminal 20, and obtains the volume data 42 of the patient KR. Based on the order information, the CT device 22 records the patient ID 46a and the examination ID 46b in the tag area 46 of each tomographic image 40 contained in the volume data 42.

The volume data 42 obtained by the CT device 22 is transmitted from the CT device 22 to the client terminal 20, and temporarily stored in the HDD 52 of the client terminal 20. The volume data 42 is transmitted to the data center 14 in response to an instruction input by the user (doctor, or the like) through the input device 54. At this time, the CPU 50 attaches the medical facility number and the like to the volume data 42, and transmits the volume data 42 to the data center 14. Timing control of the transmission is not made only by the instruction from the user. For example, the CPU 50 may transmit the volume data 42 regularly, or the data server 30 may fetch the volume data 42 at regular time intervals.

The volume data 42 transmitted to the data center 14 is input to the data server 30 via the network interface 34. The CPU 60 of the data server 30 transmits the received volume data 42 to the site recognizing section 66. The site recognizing section 66 performs image analysis of each tomographic image 40 contained in the volume data 42 and recognizes the site contained therein. Then, the site recognizing section 66 records the recognized site as the site information 46c in the tag area 46 of each tomographic image 40.

Thereafter, the site recognizing section 66 transmits the volume data 42 to the storage unit 32, and the volume data 42 is stored in the medical image DB 32d. Each volume data 42 constituted of plural tomographic images 40 is preferably stored in, for example, a dedicated folder or directory, so as to browse and manage the volume data 42 easily.

After checking the storage of the volume data 42, the CPU 60 refers to the medical facility number attached to the volume data 42 and transmits a message indicating completion of the storage to the corresponding medical facility 12. Upon receiving the message, the CPU 50 of the client terminal 20 displays a pop up message box on the monitor 53, indicating the completion of the storage, and notifies the user such as the doctor that the volume data 42 is now stored in the data center 14.

At the same time, the CPU 50 deletes the transmitted volume data 42 which has been temporarily stored in the HDD 52 to avoid a waste of the memory capacity of the HDD 52. The volume data 42 may be deleted from the HDD 52 in other timings. The volume data 42 may be deleted after a predetermined period, for example, a year, or after the treatment for the patient's injury or illness in question is completed.

After the volume data 42 is stored in the data center 14, the user transmits a transmission request of the tomographic images 40 to the data center 14 via the client terminal 20 to instruct the transmission of the tomographic images containing a desired site (target site) at the time of, for example, CT interpretation or explanation to the patient. The transmission request includes various information such as the patient ID 46a, the examination ID 46b, a desired site, the medical facility number, and the like. The user inputs these information via the input device 54 and transmits the transmission request to the data center 14.

The desired patient ID 46a and the examination ID 46b may be designated by selecting them on a list made based on the patient information and the examination information. The site is designated by selecting a desired site from a list of sites obtained by the whole-body CT scan of the patient KR. The transmission request may also contain other information.

The transmission request transmitted from the client terminal 20 is input to the data server 30 via the network 16 and the network interface 34. Upon receiving the transmission request, the CPU 60 of the data server 30 searches the medical image DB 32d and reads out the volume data 42 containing the tomographic images 40 having the same the patient ID 46a and the examination ID 46b in the tag area 46 as designated in the transmission request.

Thereafter, the CPU 60 checks the site information 46c recorded in the tag area 46 of each tomographic image 40 against the site designated by the transmission request, and extracts from the volume data 42 the tomographic images 40 in which the site indicated by the site information 46c matches the site designated by the transmission request. Thereafter, the CPU 60 refers to the medical facility number contained in the transmission request, and sets the medical facility number as a destination, and starts transmission of the extracted tomographic images 40.

As described above, the desired site is input at the time of inputting the transmission request, and only the tomographic images 40 containing the desired site are transmitted. Accordingly, it becomes possible to save the waiting time due to the transmission, and inconvenience of searching for the tomographic images 40 containing the desired site.

In the above embodiment, the site recognition is performed immediately after the data center 14 receives the volume data 42. However, the timing of the site recognition is not limited to the above. It is also possible to store the volume data 42 in the medical image DB 32d firstly, and then read the volume data 42 from the medical image DB 32d and perform the site recognition when the processing load of the CPU 60 in the data server 30 is low, for example, late at night.

Figure 6:
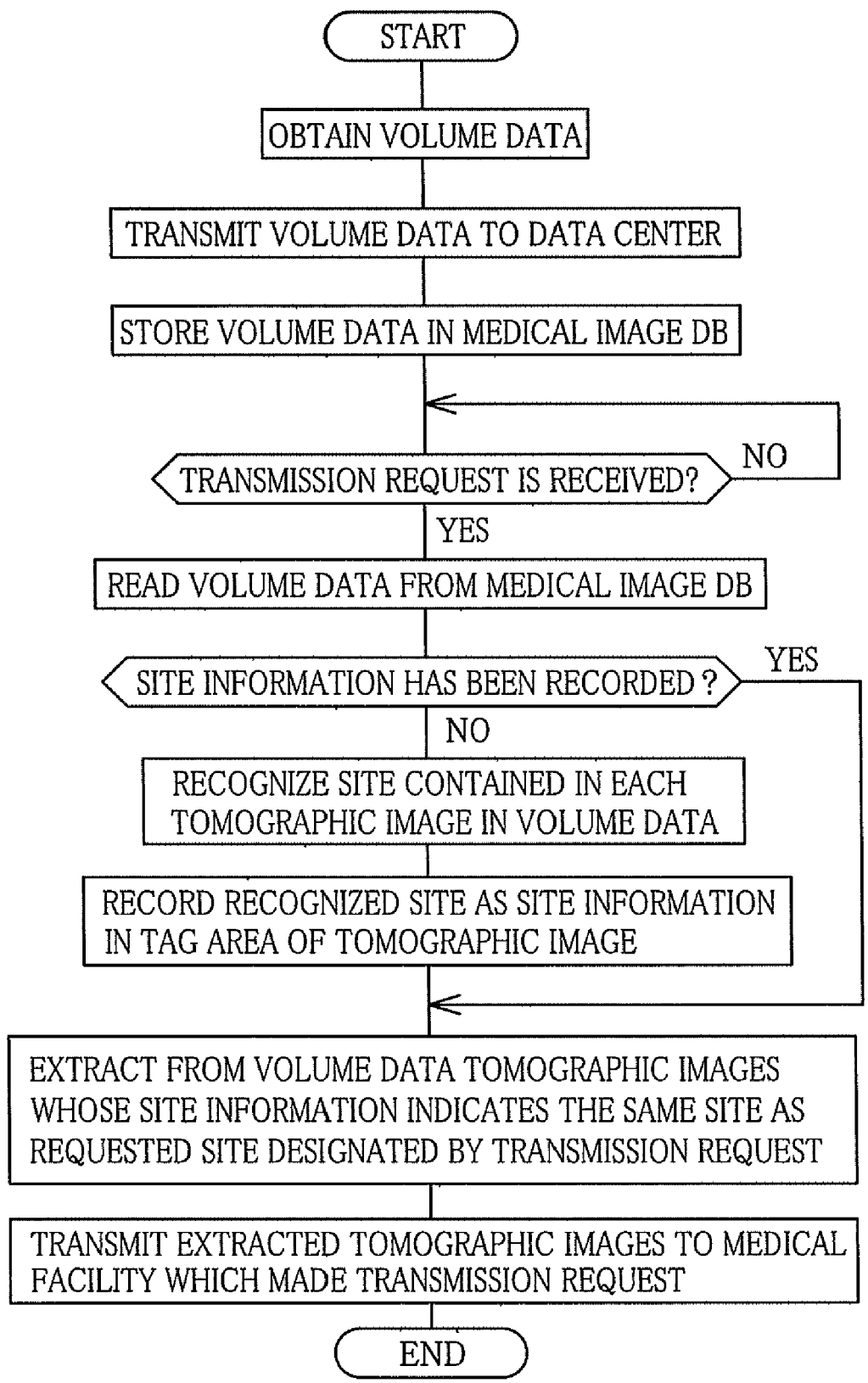
FIG. 6 is a flowchart showing an example in which site recognition is performed after a transmission request is received.
Figure 7:
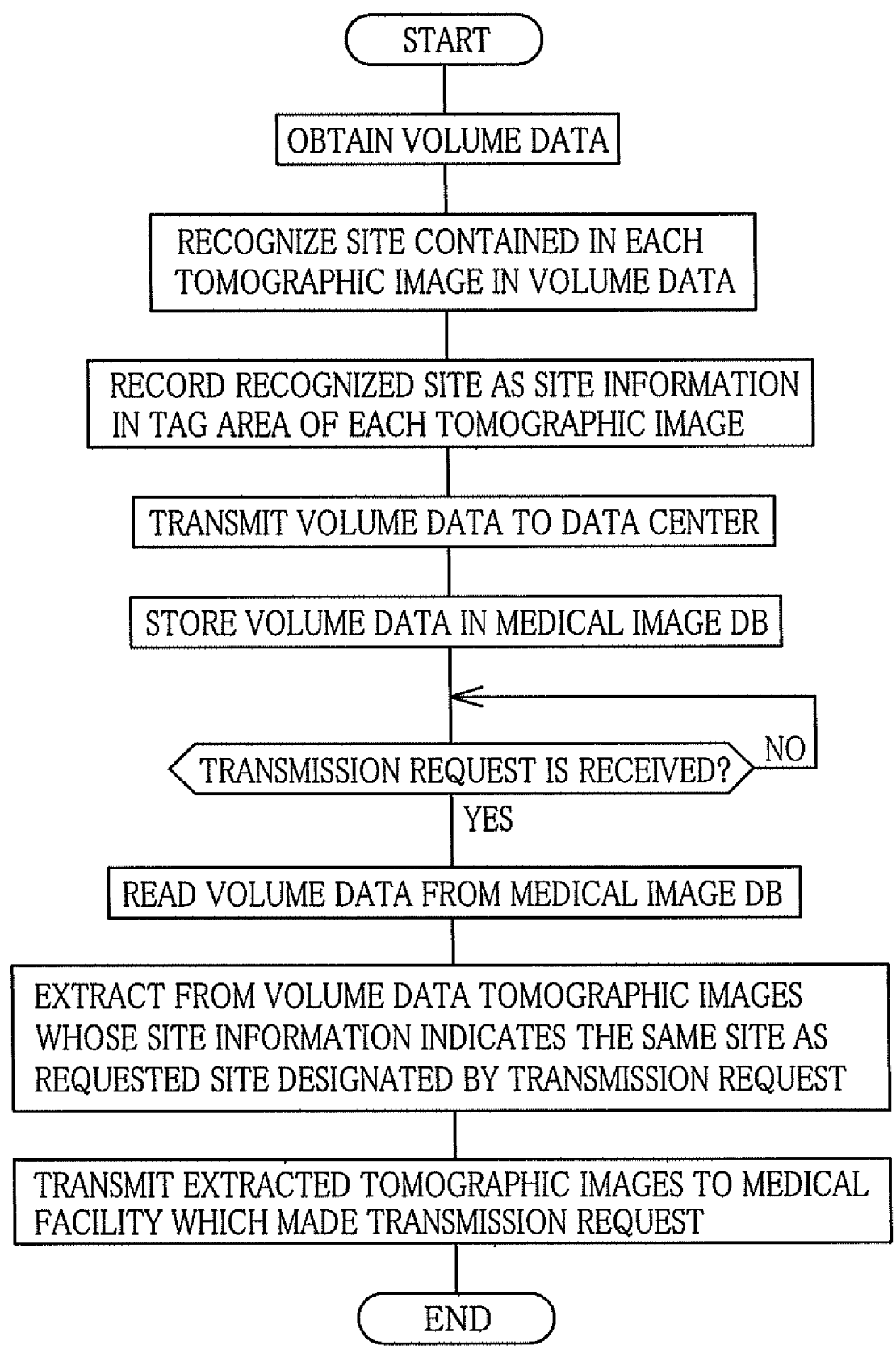
FIG. 7 is a flowchart showing an example in which the site recognition is performed at a medical facility.

As shown in a flowchart of FIG. 6, it is also possible to perform the site recognition of the tomographic images 40 after the volume data 42 is read from the medical image DB 32d in response to the transmission request from the user. In the flowchart of FIG. 6, presence or absence of the site information 46c in the tag area 46 of each tomographic image 40 is checked after the volume data 42 is read from the medical image DB 32d.

If the site information 46c has not been recorded, the CPU 60 transmits the volume data 42 to the site recognizing section 66 to recognize the site contained in each tomographic image 40 and record the site information 46c. Thereafter, the CPU 60 checks the site information 46c recorded in the tag area 46 of each tomographic image 40 against the site designated by the transmission request, and extracts from the volume data 42 the tomographic images 40 whose site information 46c indicates the same site as designated by the transmission request. If the site information 46c has been recorded, on the other hand, the CPU 60 starts the extraction processing without transmitting the volume data 42 to the site recognizing section 66. After the extraction, the CPU 60 refers to the medical facility number in the transmission request, and transmits the extracted tomographic images 40 to the medical facility 12 which made the transmission request.

As described above, even if the site recognition of each tomographic image 40 is performed after the volume data 42 is read from the medical image DB 32d in response to the transmission request from the user, it produces the same effects as the embodiment shown in the flowchart of FIG. 5. However, the embodiment shown in the flowchart of FIG. 6 may take long time to perform the site recognition if the site information 46c has not been recorded. In other words, as shown in FIG. 5, the site recognition prior to the transmission request reduces the waiting time, and is more efficient than that after the transmission request.

In the above embodiments, the site recognition is performed in the data center 14. However, the site recognition is not limited to the above. It is also possible to install the site recognizing section 66 in the client terminal 20 or the CT device 22, and perform the site recognition of each tomographic image 40 and record the site information 46c in the medical facility 12 before the volume data 42 is transmitted to the data center 14.

In the above embodiments, only the tomographic images 40 whose site information 46c indicates the same site as designated by the transmission request are extracted from the volume data 42 and transmitted. However, it is also possible to transmit the remaining tomographic images 40 in the volume data 42 after the relevant tomographic images 40 are transmitted. In this case, the completion of the transmission of the relevant tomographic images 40 is notified to the user, and then the remaining tomographic images 40 may be transmitted during the diagnosis or the like utilizing the precedingly transmitted relevant tomographic images 40, in the manner so-called background processing.

At the time of taking tomographic images 40 with the CT device 22, the site designated by the doctor or the desired site is usually included as the examination site in the order information. In the above embodiments, the desired site is included in the transmission request which instructs the transmission of the tomographic images 40. However, it is also possible to designate the examination site recorded in the examination information or the tag area 46 of the tomographic image 40 as the desired site.

In the case the desired site is the examination site, it is also possible to store only the extracted tomographic images 40 in the data center 14 as shown in the flowchart of the FIG. 8. The flowchart shows that the site recognition of each tomographic image 40 in the volume data 42 is performed by the client terminal 20 after the volume data 42 is obtained. After the site recognition, the CPU 50 of the client terminal 20 records the recognized site in the tag area 46 of the tomographic image 40 as the site information 46c. Then, the CPU 50 refers to the examination information of the corresponding examination recorded in the examination information DB 32b, or the tag area 46 of each tomographic image 40, and reads the examination site included in the order information set at the time of taking the tomographic images 40.

Thereafter, the CPU 50 checks the site information 46c recorded in the tag area 46 of each tomographic image 40 against the examination site, and extracts from the volume data 42 the tomographic images 40 whose site information 46c indicates the same site as the examination site. Then, the CPU 50 transmits the extracted tomographic images 40 to the data center 14 in response to the transmission request from the user, and stores the tomographic images 40 in the medical image DB 32d. Thus, only a portion of the volume data 42 corresponding to the examination site in the order information is stored after the whole body CT scan. Accordingly, it becomes possible to avoid a mismatch between the order information and the transmitted tomographic images, and save the waiting time and inconvenience of searching for the desired tomographic images.

In the above embodiments, the site information 46c is recorded in the tag area 46 of the tomographic image 40 as the metadata. Alternatively, it is also possible to collectively record the site information 46 in, for example, a tabular file associating each tomographic image 40 with the corresponding site.

In the above embodiments, a group of medical images is represented by the volume data 42 constituted of plural tomographic images 40 taken with the CT device 22. However, the group of medical images is not limited to the above. It is also possible to use, for example, the CR device, the MRI device, or any other modality to take the group of medical images as long as the group is constituted of plural medical images containing plural sites.

In the above embodiments, the site recognition of the medical images is automatically performed using the image analysis. However, the site recognition is not limited to the above. It is also possible to perform the site recognition by visual inspection of the doctor. In this case, the site information 46c may be input manually.

In the above embodiments, the site is recognized by the body part such as head, thorax, abdomen, pelvis, legs, or the like. However, it is also possible to recognize the site by the organ such as, for example, brain, heart, lungs, liver, or stomach. In the above embodiments, the whole body CT scan of the patient KR is carried out. However, the present invention is not limited to the above. It is also possible to take tomographic images of a part of the patient KR as long as the taken tomographic images contain plural sites.

In the above embodiments, the present invention is applied to the medical network system 10 constituted of plural medical facilities 12 and the data center 14. However, the present invention is not limited to the above configuration. The present invention is also applicable to, for example, a system constituted of plural client terminals and a data server disposed in one medical facility.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An image transmission method for transmitting only desired medical images containing a target site out of a group of medical images, said image transmission method comprising steps of:
    (a) recognizing a site contained in each said medical image;
    (b) generating site information indicating said site contained in each said medical image based on a result of said recognizing step;
    (c) extracting said desired medical images whose site information indicates the same site as said target site; and
    (d) transmitting said desired medical images to a designated destination;
    further including the steps of:
    storing said group of said medical images and said site information in a storage unit; and
    reading said group of said medical images and said site information from said storage unit in response to an instruction for said transmission;
    wherein, said storing step and said reading step are performed between said step (b) and said step (c).

2. The image transmission method of claim 1, further including the steps of:
    storing said group of said medical images in a storage unit; and
    reading said group of said medical images and said site information from said storage unit in response to an instruction for said transmission;
    wherein said storing step and said reading step are performed before said step (a).

3. The image transmission method of claim 1, further including the steps of:
    storing said extracted medical images in a storage unit; and
    reading said extracted medical images from said storage unit in response to an instruction for said transmission;
    wherein said storing step and said reading step are performed between said step (c) and said step (d).

4. The image transmission method of claim 1, wherein said target site is input concurrently with an instruction for said transmission.

5. The image transmission method of claim 1, wherein said target site is an examination site input as order information at the time of taking said group of said medical images.

6. The image transmission method of claim 1, wherein in said step (a), said site is automatically recognized by image analysis of each said medical image.

7. The image transmission method of claim 1, wherein in said step (b), said site information is attached to corresponding medical image as metadata.

8. The image transmission method of claim 1, wherein said site includes head, thorax, abdomen, pelvis, legs, and organs such as brain, heart, lungs, liver and stomach.

9. An image transmission apparatus for transmitting only desired medical images containing a target site out of a group of medical images, said image transmission apparatus comprising:
    a recognizing section for recognizing a site contained in each said medical image;
    a site information generating section for generating site information indicating said site contained in each said medical image based on a result from said recognizing section;
    an extracting section for extracting medical images whose site information indicates the same site as said target site; and
    a transmitting section for transmitting said extracted medical images to a designated destination
    further including the steps of:
    storing said group of said medical images and said site information in a storage unit; and
    reading said group of said medical images and said site information from said storage unit in response to an instruction for said transmission;
    wherein, said storing step and said reading step are performed.

10. An image transmission program stored on non-transitory computer readable medium for transmitting only desired medical images containing a target site out of a group of medical images, said image transmission program directing a computer to execute steps of:
    (a) recognizing a site contained in each said medical image;
    (b) generating site information indicating said site contained in each said medical image based on a result of said recognizing step;
    (c) extracting medical images whose site information indicates the same site as said target site; and
    (d) transmitting said extracted medical images to a designated destination; further including the steps of:
    storing said group of said medical images and said site information in a storage unit; and
    reading said group of said medical images and said site information from said storage unit in response to an instruction for said transmission;
    wherein, said storing step and said reading step are performed between said step (b) and said step (c).

* * * * *